United States Patent [19]

Weissman

[11] 4,255,145
[45] Mar. 10, 1981

[54] DENTAL TOOL HAVING SEVERABLE SECTIONS

[75] Inventor: Bernard Weissman, New York, N.Y.

[73] Assignee: IPCO Hospital Supply Corporation, White Plains, N.Y.

[21] Appl. No.: 77,399

[22] Filed: Sep. 20, 1979

Related U.S. Application Data

[63] Continuation-in-part of Ser. No. 928,557, Jul. 27, 1978, Pat. No. 4,205,444, and a continuation-in-part of Ser. No. 887,173, Mar. 16, 1978, Pat. No. 4,202,101.

[51] Int. Cl.³ .............................................. A61C 1/10
[52] U.S. Cl. .................................... 433/165; 433/128
[58] Field of Search ................................ 433/165, 128

[56] References Cited

U.S. PATENT DOCUMENTS

| | | | |
|---|---|---|---|
| 418,108 | 12/1889 | Brown | 433/165 |
| 3,343,443 | 9/1967 | Moore | 433/225 |
| 4,053,982 | 10/1977 | Weissman | 433/225 |

Primary Examiner—Robert Peshock
Attorney, Agent, or Firm—Friedman, Goodman & Teitelbaum

[57] ABSTRACT

A dental tool such as a drill, burr, anchor, reamer and the like, which is receivable in a dental tool holder, such as a dental handpiece or a hand driver, for operative positioning thereof with respect to the teeth of a patient, the dental tool having a body member provided with an operative end portion for association with the teeth and a shank extending from the operative end portion for association with the holder. The shank portion is provided with at least two cylindrical sections, each section having a circumferential groove defining a neck portion for receiving a retaining member of the tool holder for removably engaging the shank in the holder. The neck portion separates a head portion from a body portion of each section. A flat surface is formed longitudinally along one side of each section extending across the head and neck portions, and terminating along the body portion in an outwardly extending shoulder for engaging a ledge in the tool holder to thereby provide secure driving engagement between the shank and the tool holder. The cylindrical sections are spaced along the shank and provide a series of locations for driving and latching the shank in the tool holder. A circumferential notch is provided in the shank between each of the sections to permit severence of one section from the remaining sections along the shank, to thereby reduce the length of the shank for insertion into the tool holder to permit convenient access to operative areas of the patient's mouth.

10 Claims, 13 Drawing Figures

DENTAL TOOL HAVING SEVERABLE SECTIONS

RELATION TO OTHER APPLICATIONS

This application is a continuation-in-part application to co-pending application Ser. No. 928,557 filed July 27, 1978 now U.S. Pat. No. 4,205,444 issued 6/3/80 for a "Dental Tool Shank," and a continuation-in-part application to co-pending application Ser. No. 887,173 filed Mar. 16, 1978 now U.S. Pat. No. 4,202,101 issued 6/3/80 for a "Dental Anchor and A Plastic Shank For Holding Same," both of which were filed by the applicant of the present invention.

BACKGROUND OF THE INVENTION

This invention relates to dentistry in general and more particularly to a dental tool which permits a variable longitudinal extension of the shank of the tool from a tool holder associated therewith for convenient access to operative areas of the patient's mouth.

In the use of dental tools, held within a dental tool holder, it is often found that the jaw separation of the patient is inadequate to allow the tool holder carrying a suitable attachment such as a drill, burr, anchor, reamer and the like to be placed in operative position with respect to the teeth of the patient, especially the posteriors. In the vestibular area of the mouth, it has also been found that the cheek and the tongue do not readily permit access to the normal tool holder provided with conventional tool attachment extensions.

In the aforementioned co-pending application Ser. No. 928,557, there is described a dental tool having a body member provided with an operative end portion for association with the teeth of a patient and a shank extending from the operative end portion for association with a conventional dental handpiece. The shank is provided with a number of sections each of which can preferably be separated from the next adjacent section. Each section includes a circumferential groove for removably engaging the shank in a handpiece. The entire shank is provided with a flat surface along one side of the shank for driving engagement with the handpiece. In order to facilitate the severence of each section from the next adjacent one, a circumferentially tapered notch is disposed between the sections.

The dental tool described is utilized in conjunction with a dental handpiece, of the type described in my U.S. Pat. No. 3,369,298. In such dental handpiece, there is provided an aperture for receiving the shank portion. The upper portion of the aperture includes an inwardly extending flattened side against which the flat surface on the shank of the tool abuts. This flattened surface in the handpiece provides the driving engagement of the shank.

However, the lower edge of the inwardly extending flattened wall in the aperture terminates in an abutment or ledge. Since the entire length of the shank portion in the aforedescribed co-pending application has a flat surface, only the portion of the shank extending adjacent to the flat wall will be securely retained in the handpiece. However, the portion of the shank beneath the ledge or abuttment will have its flat surface spaced from the aperture in the handpiece. This spacing of the lower part of the shank may cause a vibration or wobble to occur and in some cases could make the dental tool become unlatched from the handpiece.

In the aforementioned co-pending application Ser. No. 887,173, there is described a different type of tool holder, specifically a plastic hand driver which receives the shank portion of a tool. An aperture is formed in the hand driver. At the inward end of the aperture there is again provided an inwardly directed flat wall which terminates in an abuttment. Protrusions extend from an inner portion of the aperture which are snapped into a groove formed circumferentially in the shank to retain the shank in the tool.

SUMMARY OF THE INVENTION

Accordingly, it is an object of the present invention to provide a drill, burr, anchor and the like which improves upon the aforedescribed dental tool.

Another object of the present invention is to provide a dental tool whose length can be varied to permit convenient access to the operative areas of the patient without discomfort.

Yet another object of the present invention is to provide a dental tool whose length can be varied and which tool can be securely held in a dental tool holder at each of its varied lengths.

Yet a further object of the present invention is to provide a dental tool which can be utilized in conjunction with a handpiece as well as a hand driver.

A further object of the present invention is to provide a dental tool having a shank portion with at least two sections thereon, with each section including a latching arrangement, a driving arrangement, and a securing arrangement, in conjunction with a dental tool holder.

Still a further object of the present invention is to provide a dental tool having a shank portion with at least two sections thereon, with each section including a circumferential notch for receiving a latching arrangement, a flattened surface for receiving a driving arrangement and a shoulder for effecting a securing arrangement, all within a dental tool holder.

An additional object of the present invention is to provide a dental tool which can readily be inserted into the sleeve of a dental tool holder so that a selected driving, latching, and securing arrangement is achieved at any one of a designated location along the length of the shank to thereby obtain a desired longitudinal extension of the shank from the tool holder for permitting convenient access to the operative areas of the patient's mouth.

These objects are achieved in accordance with the present invention wherein the dental tool includes a body member provided with an operative end portion for association with the teeth of a patient and a shank extending from the operative end portion for association with the dental tool holder. The shank is provided with at least two cylindrical sections. Each section includes a circumferential groove defining a neck portion for selectively receiving a retaining member of the tool holder to vary the longitudinal extension of the shank from the tool holder. Each neck portion separates the respective head portion from the respective body portion of each section. A longitudinally extending flat surface is formed along the shank of each section, crossing the respective head and neck portions of the section and terminating along its body portion in a shoulder for selectively engaging a ledge in the tool holder to provide secure driving engagement with the tool holder.

The shank further includes a circumferentially tapered notch located between the body portion of one section and the head portion of the next adjacent section for facilitating severence of one section from the next section thereby shortening the longitudinal extension of the shank to permit convenient access to operative areas of the patient's mouth.

The dental tool can be used in combination with a dental tool holder such as a handpiece or a hand driver. In each case, an aperture is formed in the tool holder for receiving the shank. A flat wall is formed along a portion of the aperture which terminates in a lower ledge. The flat wall cooperates with the flat surface of a section of the shank, and the shoulder portion of that section of the shank engages the lower ledge thereby providing the secure driving engagement of the shank. A retaining means is provided on the dental tool holder for selectively engaging one of the cylindrical grooves for retaining the shank in the tool holder.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

In the various figures of the drawing, like reference characters designate like parts.

DETAILED DESCRIPTION OF THE PREFERRED EMBODIMENTS

Figure 1:
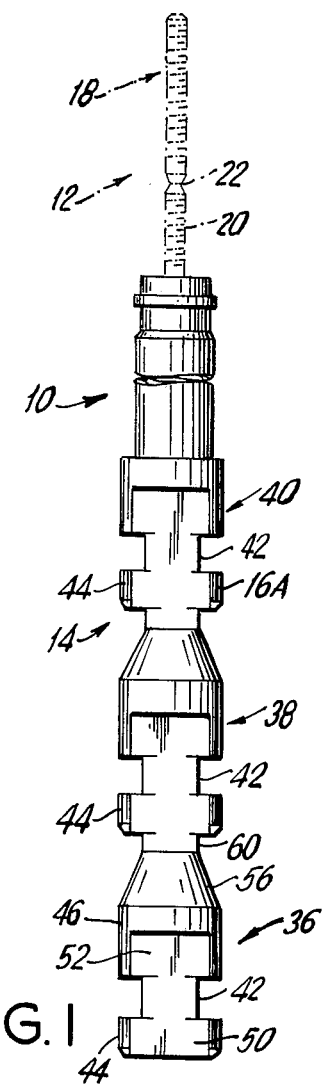
FIG. 1 is an elevational view of a dental tool, such as a dental anchor, showing the shank in accordance with the present invention.

Referring now to the drawings, FIG. 1 shows a dental tool 10 according to the present invention. The dental tool includes a dental anchor 12 provided with a body member 14 therefor, the body member 14 having a shank 16A pursuant to the present invention. The dental anchor 12 is fabricated from metal and includes two two threaded sections 18 and 20, joined by a frangible portion 22 so that the sections can be severed. The body member 14 is provided with an opening for receiving the dental anchor 12 in preferably a force-fit connection therebetween, the body member 14 being preferably fabricated from a plastic material. A similar type of construction, as described above, is disclosed in both of the aforementioned co-pending applications, to which reference may be made for a more detailed description of the function thereof, both the disclosures are herein incorporated by reference. The construction is shown for illustrative purposes only to indicate a dental tool which can be modified to include the dental tool shank of the present invention. However, it is noted that the illustrated dental anchor and body member could be formed as a one piece metal construction and still employ the shank of the present invention.

Figure 2:
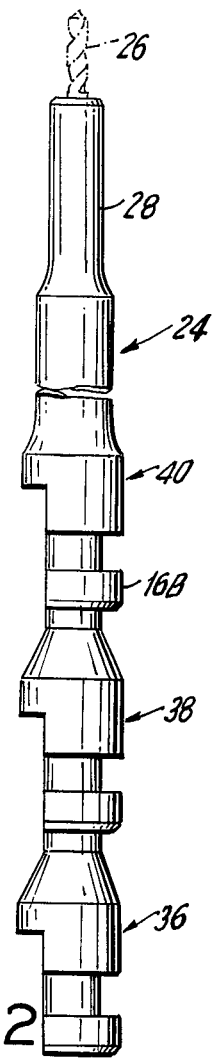
FIG. 2 is an elevational view of the dental tool, such as a dental drill, showing the shank turned 90° relative to the shank shown in FIG. 1.

FIG. 2 shows another dental tool 24 in the form of a dental drill having a dental drill bit 26 connected to the drill bit retaining body 28, both being fabricated from metal materials. The retaining body 28 is povided with a shank 16B pursuant to the present invention. A similar type of construction is disclosed in my U.S. Pat. No. 3,726,014, to which reference may be made for a more detailed description of the structure and function thereof, which description thereof is herein incorporated by reference. This type of a dental tool is shown for illustrative purposes only and in order to indicate the shank of the present invention. However, it is again noted that the drill bit and retaining body can be constructed as a one piece metal structure.

Figure 3:
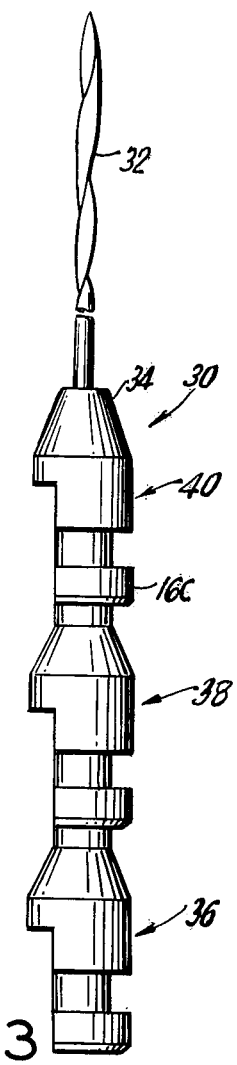
FIG. 3 is an elevational view of a dental tool, such as a reamer, showing the shank in a position similar to that shown in FIG. 2.

FIG. 3 shows yet a third dental tool 30 in the form of a reamer having a reamer bit 32 connected to a retaining body 34, both being fabricated from metal material. The retaining body 34 is provided with a shank 16C pursuant to the present invention. Again, it is noted that the reamer and the retaining body could be constructed as a one piece metal structure.

Figure 4:
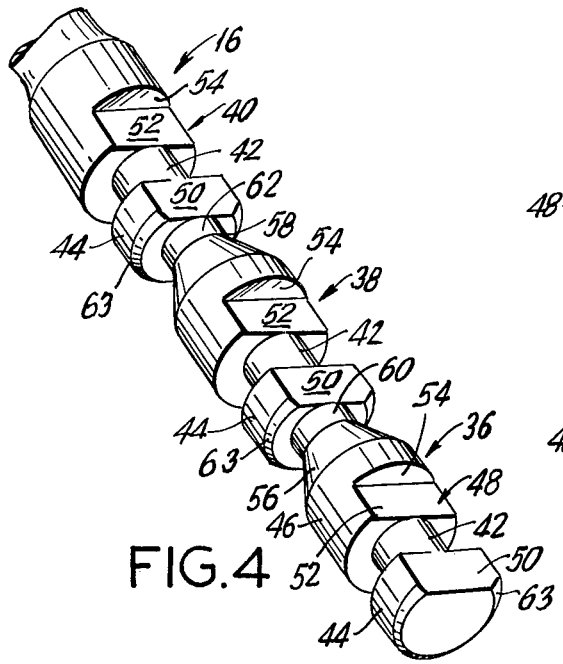
FIG. 4 is a fragmented perspective view of the shank according to the present invention.

Pursuant to the present invention, the shanks 16A, 16B and 16C, shown on the dental tools of FIGS. 1-3, are the same as is best illustrated by the shank 16 shown in FIG. 4. Accordingly, the parts of the shanks 16, 16A, 16B and 16C will now be discussed below in a more complete description, where the reference numerals for these parts will be the same for each of the shanks for a clearer and better understanding thereof.

Each of the shanks 16, 16A, 16B, 16C and the shanks of the other dental tools employing the present invention includes a plurality of substantially similar sections 36, 38, 40. Each of the sections includes a cylindrical groove forming a neck portion 42 which separates the cylindrical body of the section 36 into a cylindrical head portion 44 and a cylindrical body portion 46. A flat or planar surface 48 extending longitudinally along one side of the shank is formed in each section. The flat surface includes one flat portion 50 thereof extending transversely across the cylindrical head 44 and another flat portion 52 extending partway across the cylindrical body portion 46. The flat surface 48 terminates in an outwardly extending edge 54 thereby forming a shoulder within each section.

The flat surface 48 provides a driving engagement with a shank receiving aperture provided in the dental tool holder of a conventional handpiece or hand driver, as will hereinafter be described. The circumferential groove forming the narrow neck portion 42 receives a retaining member such as a conventional latching tongue of the handpiece or projections of the hand driver to prevent the shank from being displaced along its longitudinal axis from the handpiece or hand driver.

Additionally, the end of the body portion 46 is circumferentially tapered to provide a circumferentially tapered notch 56 spaced between adjacent sections 36 and 38. A similar notch 58 is provided between the sections 38 and 40. The notches terminate in a cylindrical collar 60 and 62, adjacent to the head portion of the next section. The notches and adjacent collars divide the shank into the plural sections 36, 38 and 40 and permit the severence of the sections from each other to limit the extension of the dental tool from the tool holder for convenient access to the operative areas of the patient's mouth without discomfort thereto.

Figure 5:
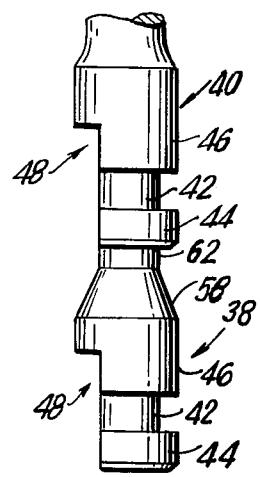
FIG. 5 is a fragmented elevational view showing the shank of FIG. 4 with one section severed therefrom.
Figure 6:
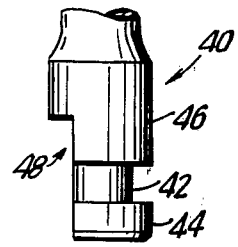
FIG. 6 is a fragmented elevational view similar to FIG. 5 showing the shank having two sections severed therefrom.

In operation, the dental tool is inserted in the tool holder and its length can be adjusted to provide the necessary convenience within the patient's mouth. For example, the dental tools shown in FIGS. 1-4 each have three sections intact. This provides for the longest extension of the dental tool. Referring now to FIG. 5, there is shown only the two sections 38 and 40 with the distal most section 36 having been severed therefrom. FIG. 6 shows only the section 40 with both the previous two sections 36 and 38 having been severed therefrom. Each of the sections may be severed from the remainder of the shank by the use of a suitable cutting tool, such as snips or pliers well known in the art, in the case of a metal shank; or in the case of a plastic shank, a razor blade may be used to sever the desired sections.

Although only three sections have been shown, it is of course understood that any number of sections may be provided on the shank 16 which may be suitably severed to any desired length. Furthermore, this arrangement may be provided on the shank of any suitable tool presently used with a conventional handpiece or hand driver, or may be fabricated from any material that may be developed, where any suitable cutting tool may be employed for achieving the severance along the selective notch which acts as a guide for such cutting.

Preferably, the edge of the head portions 44, at the remote end and those edges facing toward the next adjacent collar 60, is formed with a peripheral level 63.

Figure 7:
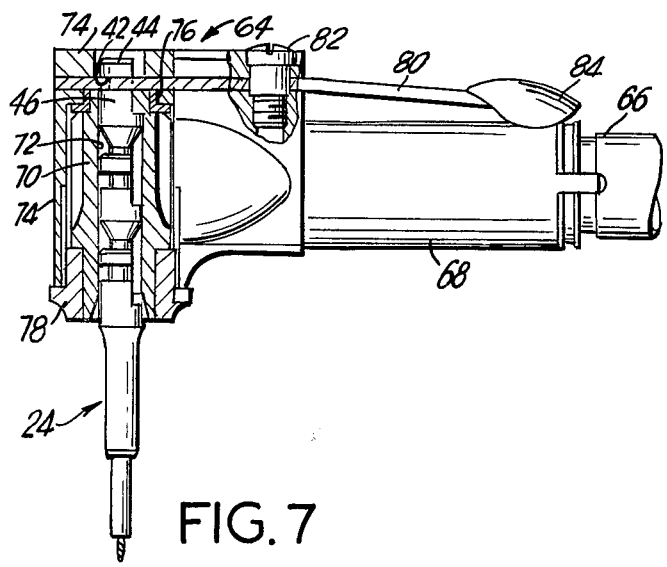
FIG. 7 is a fragmented elevational view showing the dental drill of FIG. 2 disposed in a conventional dental handpiece illustrating the tool in its longest position.
Figure 8:
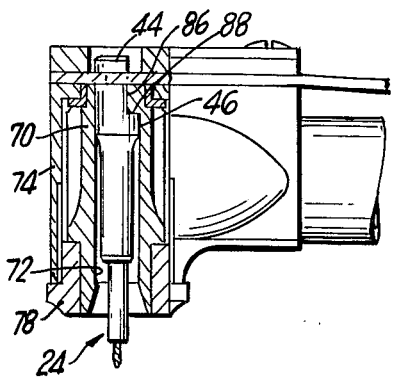
FIG. 8 is a view similar to FIG. 7 and illustrating the dental tool shank in its shortest position.
Figure 10:
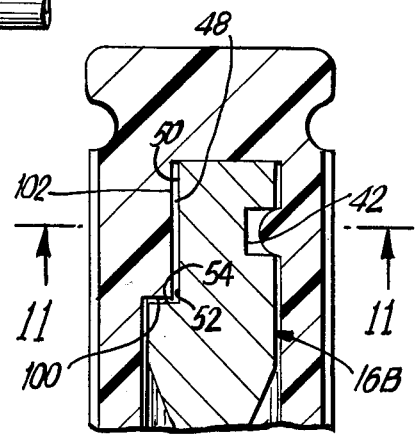
FIG. 10 is a cross sectional view taken along line 10—10 of FIG. 9.

Referring now to FIGS. 7 and 8, there is shown a dental tool 24 of FIG. 2 disposed in a conventional head portion 64 of a conventional dental handpiece, to illustrate the variable length of the dental tool shank with respect to the dental handpiece, pursuant to the present invention. Additionally, it shows the feature of providing the securing shoulder within each section to prevent vibration or wobble of the dental tool in the dental holder. The particular dental handpiece is of a type described in the aforementioned U.S. Pat. No. 3,369,298, the entire disclosure of which is herein incorporated by reference.

The tool holder includes a coupling member 66 which is adapted to receive the chuck end of the handpiece (not shown). The coupling member mounts a drive shaft which is gripped by the chuck of the handpiece so that it can be rotated by the dental engine. The tubular sleeve 68 is provided with a worm gear (not shown) which is connected to a pinion gear 70 positioned to surround an aperture 72 in the housing 74 of the handpiece. A bushing 76 is positioned above the pinion gear. The pinion gear is retained in position within the housing 74 by means of a threaded nut or plug 78 which is releasably engaged within the housing.

In order to lock the tool in the pinion gear, provision is made for the lock 80. The lock is pivotally mounted by means of the pivot screw 82 disposed in the housing 74. The lock is provided with a finger piece 84 whereby it may be pivotally moved from its operative locking position to its operative unlocked position. The lock is provided with a locking slot which is adapted to engage the neck portion 42 of the shank with the head portion 44 extending thereabove and the body portion 46 extending therebeneath.

Within the upper end of the aperture, there is formed an inwardly directed flat wall 86 which is adapted to receive the flat portion 52 of the flat surface 48 of the shank. The lower end of the flat wall 86 terminates in an inwardly directed abuttment or ledge 88 against which the shoulder 54 of the shank abuts.

As shown in FIG. 7, the dental tool 24 is inserted in the dental handpiece and is secured by the lock 80. Thus, the shank extends its full limit from the dental handpiece with all three sections being intact. When it is desired to reduce the tool extension to accommodate the limitations of a patient's mouth, the dentist may sever the upper one or two sections from the shank by the use of a suitable cutting tool as set forth above. FIG. 8 illustrates the dental tool 24 secured in the dental handpiece with the upper two sections severed therefrom.

In the previously described co-pending application Ser. No. 928,557, the flat surface extends the entire length of the shank. Accordingly, with any sections more than the lowermost section remaining intact on the shank, the flattened surface would extend into the lock 80 so that the lock would engage the neck portion. The flat portion would extend completely downwardly through the entire aperture. However, beneath the ledge 88, the aperture widens as compared to the upper portion. If the entire length of the shank had the flattened portion, then it would be spaced from the aperture walls and there might be a tendency of the tool to wobble. With the present invention, each section has its own shoulder which abuts against the abuttment or ledge 88. Furthermore, beneath the shoulder, in each section, the body portion 46 is wide for accommodating the full circumference of the shank and substantially filling the aperture so as to prevent vibration or wobble of the tool in the aperture of the handpiece. This shoulder provides a securing mechanism for each section of the shank to prevent such wobble.

Figure 9:
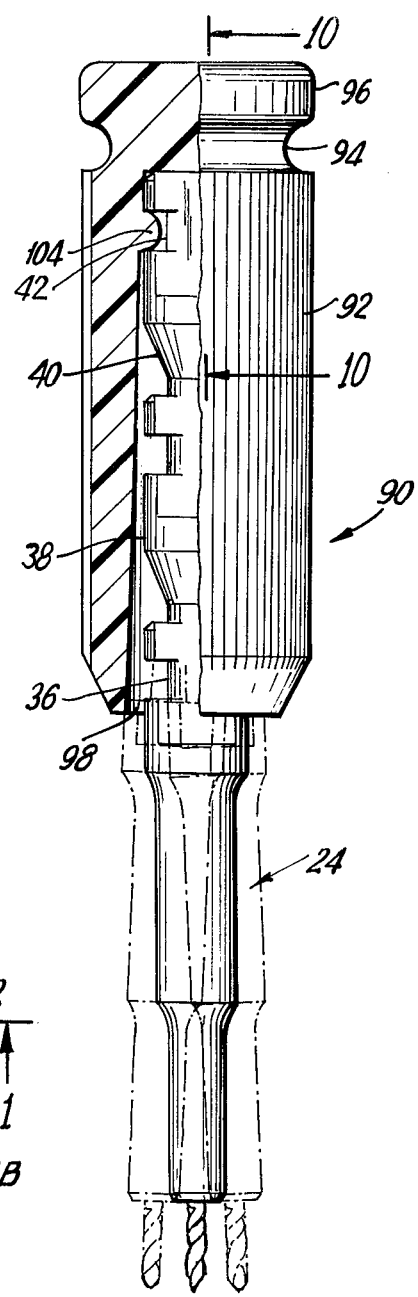
FIG. 9 is an elevational view, partly in section, showing a hand driver of the present invention receiving the dental drill of FIG. 2.

In addition to utilizing the dental tool in a handpiece as shown in FIGS. 7 or 8, it is possible to utilize the dental tool also in a hand driver of the type described in the aforementioned co-pending application Ser. No. 887,173. Referring now to FIG. 9, there is shown the hand driver 90 of the present invention, which is fabricated from a plastic material. A major portion of the outside surface of the hand driver is knurled at 92 in a longitudinal direction to aid in the hand rotation thereof. The upper end is provided with a transverse groove 94 and a smooth unknurled end 96. In use, the dentist preferably ties one end of a cord, such as dental floss, within the groove 94 and the other end of the cord or dental floss around his fingers so that in case the hand driver, which is small in size, slips from his grip, the cord will prevent the hand driver 90 from falling down the patient's throat. At the lower end of the hand driver 90, an opening 98 extends longitudinally inwardly therefrom for receiving any one of the above mentioned dental tools. The longitudinal opening 98 is tapered to facilitate the insertion of the shank, and to permit pivotal movement as set forth below.

An inner end of the opening 98 is provided with an abuttment or shelf 100. The abuttment forms the lower ledge of the inwardly extending flat surface 102 which receives both flat portions 50 and 52 of the flat surface 48 of the shank 16B when inserted within the hand driver. The shoulder 54 abuts against the shelf 100. The flat surfaces 48 and 102, adjacent to each other, provide the rotation of the shank along with the hand driver. The abutting shoulder 54 against the shelf 100 provides for a secure relationship therebetween.

Figure 11:
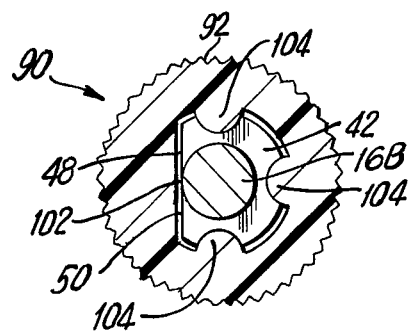
FIG. 11 is a cross sectional view taken along line 11—11 of FIG. 10.

Additionally, projections or raised curved portions 104, extend into an inner portion of the opening 98. Accordingly, these projections are snapped into the neck portion 42 of the shank 16B to retain the shank 16B within the hand driver 90. As best shown in FIG. 11, preferably three projections 104 extend around the neck portion 42 of the shank 16B.

As shown in FIG. 9, the curvature of the projections 104, permits a pivotal relationship between the shank 16B and the hand driver 90 as indicated in phantom lines. The tapering of the opening 98 also permits the pivotal movement between the shank and the hand driver. Thus, the dentist is provided with a pivotal movement between the hand driver and the shank. This permits a slight bending or flexure of the shank in order to obtain a proper alignment of the dental tool with respect to the tooth.

Figure 12:
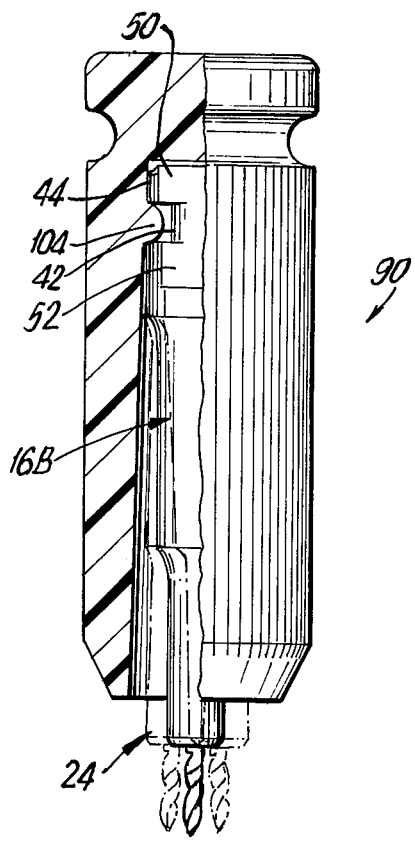
FIG. 12 is a view similar to that of FIG. 9 showing the dental tool shank in its shortest length position.

The dental tool as shown in FIG. 9 has all of its sections 36, 38 and 40 connected, whereby the tool extends in its greatest length from the hand driver. As heretofore explained, the length of the dental tool can be adjusted by severing sections from the distal end as is needed. As can be seen in FIG. 12, the tool 24 has the sections 36 and 38 severed therefrom with only the section 40 retained. The section 40 will also be maintained within the hand driver by means of the projections 104 extending into its neck 42 and with the flat portion 50 and 52 against the flat wall 102 to provide the necessary driving force. Similarly, there will also be provided the interconnection between the shoulder 54 and the abuttment 100 to provide the securing force needed to retain the dental tool in place.

Figure 13:
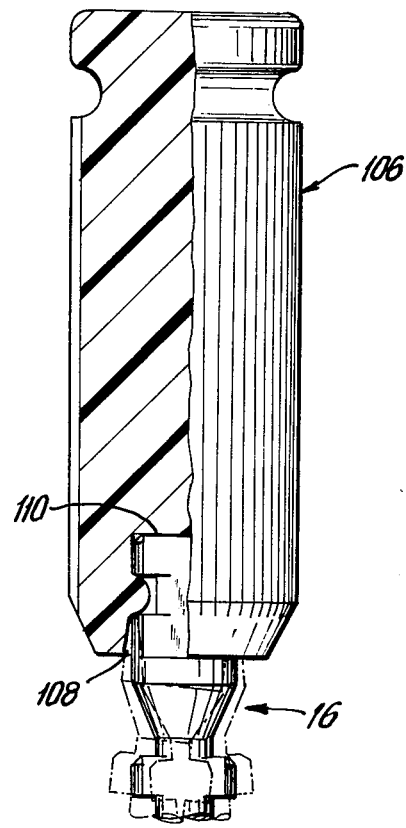
FIG. 13 shows another hand driver having a shallow aperture in its front end and receiving a shank in accordance with the present invention.

Referring now to FIG. 13, there is shown a further hand driver 106, similar in construction to the driver 90, however, the opening 108 is shallow having its rear wall 110 extending only partway into the hand driver 106. Such hand drivers with shallow openings also can be utilized with the above mentioned dental tools when a slightly greater extension is permissible and desired.

Numerous alterations of the structure hereindisclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental tool such as a drill, burr, anchor, reamer and the like, which is receivable in a dental tool holder for operative positioning thereof with respect to teeth of a patient, said dental tool comprising:
   a body member being provided with an operative end portion for association with the teeth and a shank extending from the operative end portion for association with the tool holder;
   said shank including at least two cylindrical sections, each section having a circumferential groove defining a neck portion for selectively receiving a retaining member of the hand tool according to a selected longitudinal extension of said shank from the hand tool, each neck portion separating a respective head portion from a respective body portion of each section; and
   a longitudinally extending flat surface disposed along each section crossing the respective head and neck portions of the associated section and terminating along its respective body portion in a shoulder for selectively engaging a ledge in the tool holder to provide secure driving engagement with the tool holder, said shank further including frangible means located between the body portion of one section and the head portion of the next adjacent section for facilitating severence of one section from the next section thereby shortening the longitudinal extension of said shank to permit convenient access to operative areas of the patient's mouth.

2. A dental tool as in claim 1, wherein said frangible means is a circumferential tapered notch disposed at the end of each body portion.

3. A dental tool as in claim 2, and further comprising a circumferential collar at the end of each tapered notch.

4. A combination of a dental tool, such as a drill, burr, anchor, reamer and the like, and a dental tool holder, for rotating said dental tool which is receivable in said dental tool holder for operative positioning therewith with respect to teeth of a patient, said combination comprising:
   said dental tool including a body member provided with an operative end portion for association with the teeth and a shank extending from the operative end portion for association with said dental tool holder;
   said shank comprising at least two cylindrical sections, each section including a circumferential groove and a flat surface on one side of said shank terminating in a transverse shoulder portion;
   said dental tool holder including an aperture for receiving said shank, a flat wall provided along a portion of said aperture and terminating in a lower ledge and selectively cooperating with said flat surface and said shoulder portion of each shank section for providing secure driving engagement to said shank, and retaining means for selectively engaging one of said cylindrical grooves in said sections for retaining said shank in said aperture, said shank further including frangible means located between said sections for facilitating severence of one section from the next section for shortening the longitudinal extension of said shank to permit convenient access to operative areas of the patient's mouth.

5. The combination as in claim 4, wherein said frangible means is a circumferential tapered notch disposed between said sections.

6. The combination as in claim 5, and further comprising a circumferential collar at the end of said tapered notch.

7. The combination as in claim 4, wherein said dental tool holder is a dental handpiece, and wherein said retaining means is a latching member for locking onto the selected circumferential groove.

8. A combination as in claim 4, wherein said dental tool holder is a hand driver, and wherein said retaining means comprises means for releasably retaining said shank while permitting a pivotal relationship between said shank and said hand driver when said dental tool is rotated in the tooth.

9. A combination as in claim 8, and wherein said retaining means comprises projections extending into an inner portion of said aperture, said projections being snapped into said circumferential groove to retain said shank while permitting pivotal movement therebetween.

10. A combination as in claim 9, wherein said aperture of said hand driver has a tapered portion leading therefrom for guiding said shank into said hand tool aperture and for permitting said pivotal movement.

* * * * *